(12) United States Patent
Kato et al.

(10) Patent No.: US 9,023,120 B2
(45) Date of Patent: May 5, 2015

(54) FUEL PRODUCTION METHOD, FUEL PRODUCTION APPARATUS, AND FUEL OIL

(75) Inventors: Atsushi Kato, Aichi (JP); Shigeji Tsuta, Aichi (JP); Hirohide Horibe, Aichi (JP)

(73) Assignee: Cyuba Enzyme Ltd., Okazaki-shi, Aichi (JP)

( * ) Notice: Subject to any disclaimer, the term of this patent is extended or adjusted under 35 U.S.C. 154(b) by 517 days.

(21) Appl. No.: 12/777,769

(22) Filed: May 11, 2010

(65) Prior Publication Data
US 2010/0319241 A1 Dec. 23, 2010

Related U.S. Application Data (63) Continuation of application No. PCT/JP2009/006222, filed on Nov. 19, 2009.

(30) Foreign Application Priority Data

Jun. 19, 2009 (JP) .................................. 2009-146671

(51) Int. Cl.
- C10L 1/32 (2006.01)
- C12P 1/00 (2006.01)
- C10L 1/04 (2006.01)
- C12N 9/90 (2006.01)
- C12N 9/42 (2006.01)

(52) U.S. Cl.
CPC ... *C10L 1/04* (2013.01); *C12N 9/90* (2013.01); *C12N 9/2437* (2013.01)

(58) Field of Classification Search
CPC ....... C10L 1/1802; C10L 1/1857; C10L 1/02; C10L 1/045; C11C 1/045; C11C 3/003; C11B 13/04; C12N 9/2437; C12N 9/90; Y02E 50/343; Y02E 50/10
USPC ..................... 44/301, 605; 208/236
See application file for complete search history.

(56) References Cited

U.S. PATENT DOCUMENTS

| | | | | | |
|---|---|---|---|---|---|
| 3,005,624 | A | * | 10/1961 | Weinbrenner et al. | 366/195 |
| 3,420,506 | A | * | 1/1969 | Gurley, Jr. | 366/317 |
| 3,847,800 | A | * | 11/1974 | Guth et al. | 208/236 |
| 5,697,986 | A | * | 12/1997 | Haas | 44/308 |
| 5,980,733 | A | * | 11/1999 | Collins et al. | 208/236 |
| 2005/0084941 | A1 | * | 4/2005 | Abe et al. | 435/135 |
| 2009/0217571 | A1 | * | 9/2009 | Singh et al. | 44/385 |
| 2010/0227042 | A1 | * | 9/2010 | Penet et al. | 426/655 |

FOREIGN PATENT DOCUMENTS

| | | | |
|---|---|---|---|
| CN | 1172845 | * | 2/1998 |
| CN | 1210134 | * | 3/1999 |
| JP | 04-071118 A | | 3/1992 |
| JP | 2002-233393 A | | 8/2002 |
| JP | 2009-091593 A | | 4/2009 |

OTHER PUBLICATIONS

Machine Translation of Zhu (CN 1210134).*
Machine Translation of Yang (CN 1172845).*
Patent Abstracts of Japan, Publication No. 04-071118, Publication Date: Mar. 5, 1992, 1 page.
Patent Abstracts of Japan, Publication No. 2009-091593, Publication Date: Apr. 30, 2009, 1 page.
Patent Abstracts of Japan, Publication No. 2002-233393, Publication Date: Aug. 20, 2002, 1 page.

* cited by examiner

*Primary Examiner* — Ellen McAvoy
*Assistant Examiner* — Ming Cheung Po
(74) *Attorney, Agent, or Firm* — Osha • Liang LLP (57) ABSTRACT

A fuel production method and a fuel production apparatus, for producing fuel by which the fuel efficiency can be improved and the generation of hazardous substances can be easily suppressed and which is stable, and fuel oil produced by such a method and apparatus are provided. This improves the satisfaction of users, and contributes to the prevention of environmental destruction.

A fuel production method for producing fuel oil by mixing and reacting enzyme water with petroleum-based hydrocarbon oil is provided, the enzyme water being produced by mixing a natural plant enzyme, containing at least lipase, in water. The natural plant enzyme further contains cellulase. The enzyme water further contains methanol.

4 Claims, 14 Drawing Sheets

| ITEM | SULFUR OXIDE | METAL OXIDE (ASH) | WATER | CARBON REMAINING IN CO2 | KINETIC VISCOSITY | POUR POINT | FRASH POINT |
|---|---|---|---|---|---|---|---|
| MASS·UNIT | % | % | % | % | cst mm$^2$/s | °C | °C |
| JIS | 2.0 OR LOWER | 0.05 OR LOWER | 0.3 OR LOWER | 4.0 OR LOWER | 20 OR LOWER | 5 OR LOWER | 60 OR HIGHER |
| E. C. O. CLEAN OIL | 0.74 | 0.001 | 0.01 | 0.02 | 2.92 | -12.5 | 71 |
| IMPROVING RATIO | 63.0 | 98.0 | 96.67 | 99.50 | 85.4% | USABLE IN A COLD DISTRICT WITH OUTDOOR TEMPERATURE OF -20°C | SAFETY IMPROVED BY 11°C |

FUEL PRODUCTION METHOD, FUEL PRODUCTION APPARATUS, AND FUEL OIL

BACKGROUND OF THE INVENTION

1. Field of the Invention

The present invention relates to a fuel production method and a fuel production apparatus for producing fuel, which, for example, provides a good fuel efficiency and prevents environmental destruction, and fuel oil produced by such a method and apparatus.

2. Description of the Prior Art

Mankind uses various types of energy such as fossil fuel, bioenergy, solar energy and the like. Among these types of energy, fossil fuel has been used for many years worldwide, and therefore, is precious.

Today, meanwhile, there is a problem of environmental destruction caused by energy. It is known that fossil fuel contains a sulfur component, a nitrogen component and a phenol component which generate hazardous gas leading to environmental destruction. It is also an urgent task to take a measure against global warming caused by the generation of $CO_2$.

In order to prevent or suppress the environmental destruction, it is effective to reduce the generation of hazardous gas which is caused by use of fossil fuel and to improve the fuel efficiency.

As a technology for realizing this, an emulsifier for water-in-oil emulsion fuel has been proposed (see Patent Document 1). The emulsifier for water-in-oil emulsion fuel contains A heavy oil, B heavy oil, C heavy oil, methanol, dextrin, and water. The emulsifier is mixed with petroleum fuel and water to form petroleum emulsion fuel. It is described that owing to this, the combustion efficiency can be improved and the generation of hazardous waste such as nitrogen oxide, soot or the like can be prevented.

Another type of water-in-oil emulsion fuel, which contains A heavy oil, B heavy oil, C heavy oil, methanol, ethanol, palm oil and water has also been proposed (see Patent Document 2). This water-in-oil emulsion fuel is also described to improve the fuel efficiency and reduce the generation of hazardous waste.

PRIOR ART DOCUMENT

Patent Document

Patent Document 1 Japanese Laid-Open Patent Publication No. 4-71118
Patent Document 2 Japanese Laid-Open Patent Publication No. 2009-91593

Problems to be Solved by the Invention

However, the above-described conventional technologies both have a problem that the water-in-oil emulsion fuel produced by the technologies lack stability. In more detail, the water-in-oil emulsion fuel is produced by stirring and mixing, which involves problems that oil and water may be separated from each other and that an accidental fire may occur, while the fuel is transported through a pipeline or the like.

SUMMARY OF THE INVENTION

The present invention, made in light of the above-described problems, has an object of providing a fuel production method and a fuel production apparatus for producing fuel by which the fuel efficiency can be improved and the generation of hazardous substances can be easily suppressed and which is stable, and fuel oil produced by such a method and apparatus; and also of improving the satisfaction of users and contributing to the prevention of environmental destruction.

Means for Solving the Problems

The present invention is directed to a fuel production method for producing fuel oil by mixing and reacting enzyme water with petroleum-based hydrocarbon oil, the enzyme water being produced by mixing a natural plant enzyme, containing at least lipase, in water.

Owing to this, the post-reaction water also acts as fuel, and so the fuel efficiency can be improved.

In one embodiment of the present invention, the natural plant enzyme may preferably further contain cellulase.

The enzyme water may further contain methanol mixed therein.

In one embodiment of the present invention, for mixing and reacting the enzyme water with the petroleum-based hydrocarbon oil, the enzyme water and the oil may be caused to pass through a conical stirrer, having a plurality of pins provided therein, in a whirlwind manner.

Owing to this, the reaction of the enzyme water and the oil can be promoted.

In one embodiment of the present invention, residue may be removed from the fuel oil to produce refined fuel oil. Owing to this, impurities can be removed to obtain highly pure refined fuel oil.

The present invention is also directed to a fuel production apparatus for producing fuel oil by reacting enzyme water with petroleum-based hydrocarbon oil in a decomposing reaction tank, the enzyme water containing a natural plant enzyme, which contains at least lipase, mixed therein, the fuel production apparatus comprising a stirrer in the decomposing reaction tank, wherein the stirrer has a plurality of pins standing on an inner surface defining a conical shape, an inflow opening for the enzyme water and the petroleum-based hydrocarbon oil provided in a side surface of a base part of the conical shape, and a discharge opening for the enzyme water and the petroleum-based hydrocarbon oil provided at an apex part or the center of the base part of the conical shape.

Owing to this, fuel oil having a high fuel efficiency can be produced because the post-reaction water also acts as fuel.

In one embodiment of the present invention, the inflow opening of the stirrer may be located eccentrically such that an inflow direction of the enzyme water and the petroleum-based hydrocarbon oil is eccentric with respect to the center of a circle of the conical shape.

Owing to this, the liquid can be rotated easily in the stirrer, and can be easily stirred in a whirlwind manner.

In one embodiment of the present invention, the fuel production apparatus may comprise a residue removing section for removing residue from the fuel oil produced in the decomposing reaction tank to produce refined fuel oil.

Owing to this, impurities can be removed to obtain highly pure refined fuel oil.

In one embodiment, the present invention can also provide fuel oil produced by mixing and reacting enzyme water with petroleum-based hydrocarbon oil, the enzyme water being produced by mixing a natural plant enzyme, containing at least lipase, in water.

Effect of the Invention

The present invention can provide a fuel production method and a fuel production apparatus for producing fuel oil by which the fuel efficiency can be improved and the generation of hazardous substances can be easily suppressed and which is stable, and fuel oil produced by such a method and apparatus, and also can improve the satisfaction of users and contribute to the prevention of environmental destruction.

DESCRIPTION OF THE PREFERRED EMBODIMENTS

An embodiment of the present invention will be described with reference to the drawings.

Example

Figure 1:
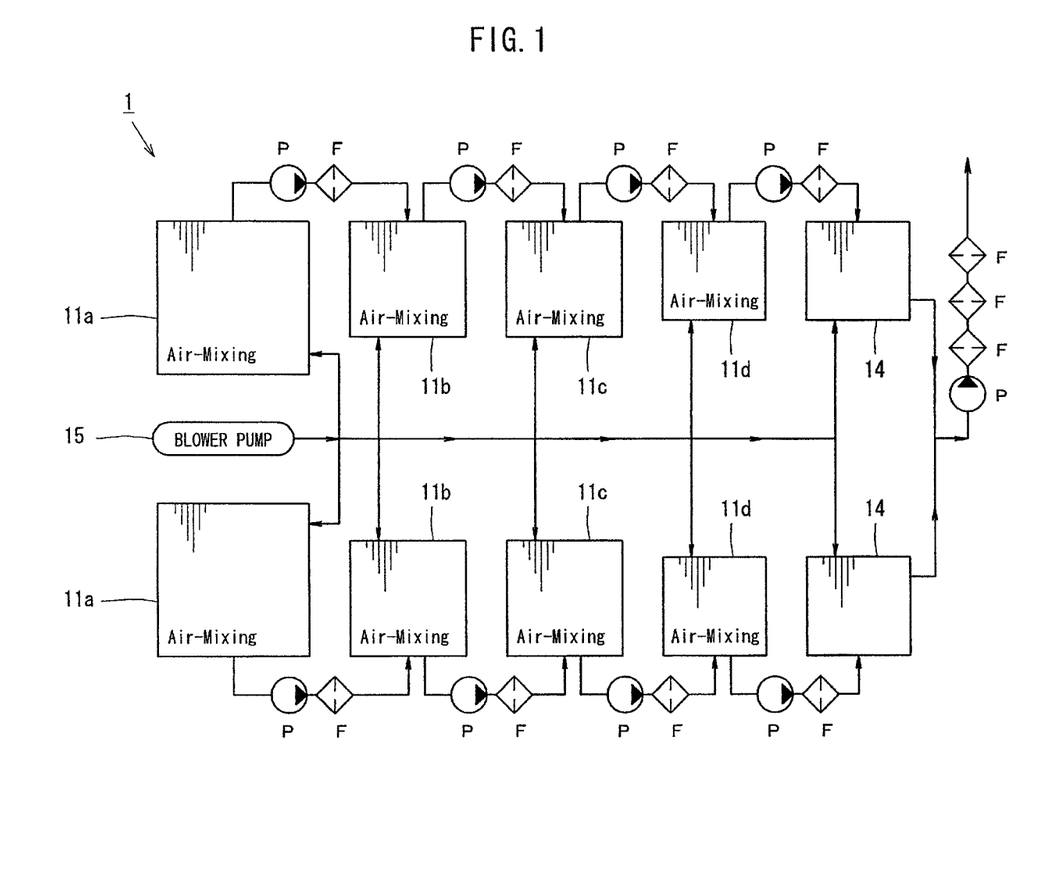
FIG. 1 is a structural view of an enzyme water production apparatus for producing enzyme water.

FIG. 1 is a structural view of an enzyme water production apparatus 1 for producing enzyme water.

The enzyme water production apparatus 1 includes a plurality of mixing tanks 11 (11a through 11d), stabilizing tanks 14, a blower pump 15 for sending air to each of the tanks, pumps P for transferring a liquid between the tanks, and filters F for removing impurities during the transfer.

The mixing tanks 11a through 11d are provided in two systems as shown in top and bottom parts of the figure, and the mixing tanks 11a through 11d in each of the systems are connected in series by the pumps P and the filters F.

Each mixing tank 11a is supplied with soft water and enzyme powder (for example, EP-10), and the soft water and the enzyme powder are stirred and mixed by air supplied from the blower pump 15. A preferable ratio of the water and the enzyme powder is, for example, approximately 0.05% (weight ratio) of the enzyme powder with respect to 99.95% (weight ratio) of the soft water. Preferably, the enzyme powder is formed of a vegetable-derived enzyme (natural plant enzyme), and especially preferably of a fruit-derived enzyme. Preferably, the enzyme contains lipase as a main component, and more preferably is formed of lipase and cellulase. It is also preferable that the enzyme contains bivalent iron oxide. It is more preferable that the enzyme contains 98% (weight ratio) of lipase and 2% (weight ratio) of cellulase. Such an enzyme can be extracted from fruits such as mango, avocado, pineapple, noni, seabuckthorn and the like. Preferably, the enzyme powder is obtained by thermally drying such an enzyme and used with improved preservability.

The resultant water mixture is transferred to the next mixing tank 11b by the pump P after a certain time period. During the transfer, impurities are removed by the filter F. In the mixing tank 11b, the water and the enzyme powder are again stirred and mixed by air supplied from the blower pump 15. This cycle is repeated until being finished in the mixing tank 11d, and alcohol is added in the stabilizing tank 14. The alcohol may be, for example, methanol or ethanol, and methanol is preferable. A preferable ratio of the alcohol is, for example, about 10% to 20% (weight ratio) of methanol with respect to the water mixture.

The enzyme water refined with alcohol is taken out from the stabilizing tank 14 by the pump P. During this process, impurities are removed by three filters F. The refined enzyme water which is taken out is transferred to a different appropriate container or stored in an enzyme water tank 22 of a fuel production apparatus 2 shown in FIG. 2.

Figure 2:
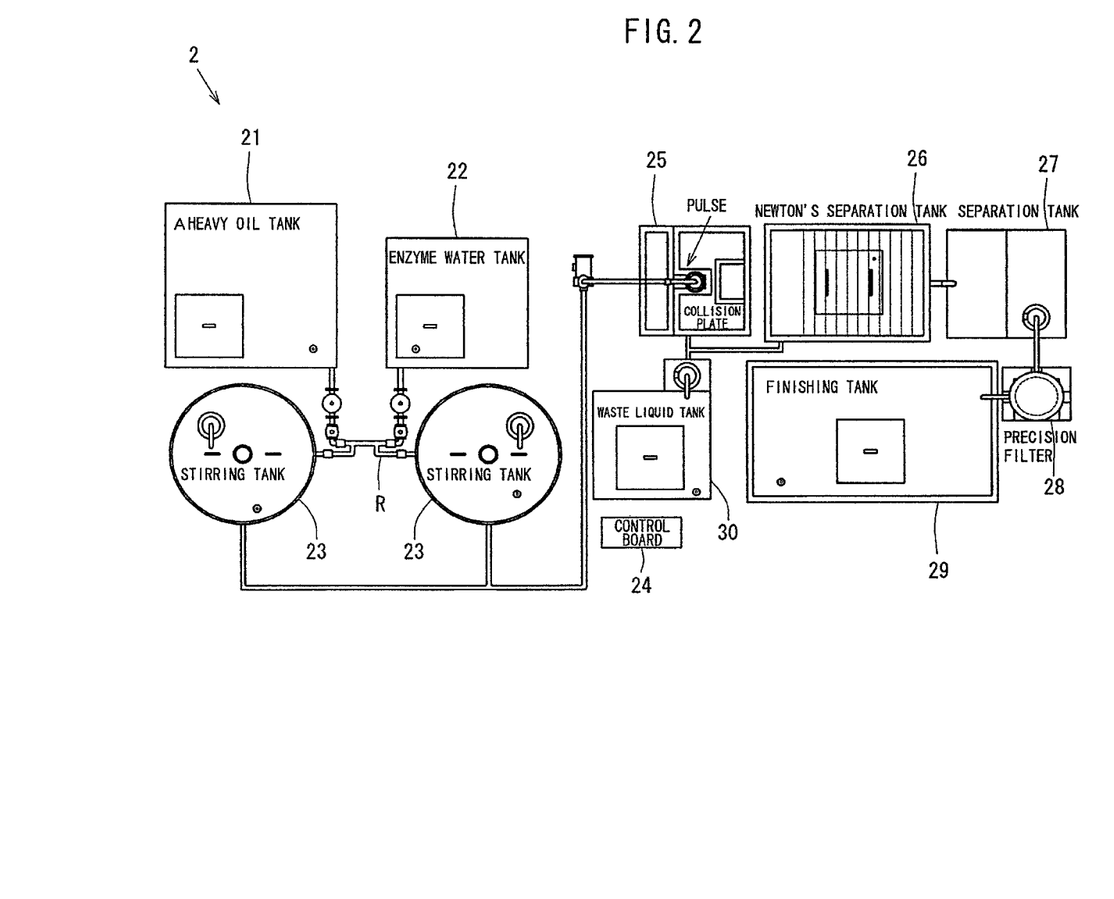
FIG. 2 is a structural view of a fuel production apparatus.

FIG. 2 is a structural view of the fuel production apparatus 2.

The fuel production apparatus 2 includes a material oil tank 21 as an oil storage section for storing oil, the enzyme water tank 22 as an enzyme water storage section for storing enzyme water, two stirring tanks 23, a control board 24, a pulse adding section 25, a Newton's separation tank 26, a separation tank 27, a precision filter section 28, a finishing tank 29, and a waste liquid tank 30.

The material oil tank 21 is a tank for storing oil used as a material, and injects the material oil stored therein by a unit of necessary amount into the stirring tanks 23 through a pipe R. The material oil may be, for example, A heavy oil, B heavy oil, C heavy oil, light oil, kerosene or the like. In this example, A heavy oil is used.

The enzyme water tank 22 is a tank for storing enzyme water refined by the enzyme water production apparatus 1, and injects the enzyme water stored therein by a unit of necessary amount into the stirring tanks 23 through the pipe R.

The stirring tanks 23 are each a tank for producing fuel oil by stirring and thus reacting the injected material oil (in this example, A heavy oil) with the injected enzyme water. The reaction here is a hydrolysis reaction of the material oil by the enzyme. The ratio of the material oil and the enzyme water to be injected into the stirring tanks 23 may be appropriately adjusted in accordance with the type of the material oil. For example, a preferable ratio is 60% of A heavy oil and 40% of the enzyme water, 70% of light oil and 30% of the enzyme water, or 70% of kerosene and 30% of the enzyme water.

The control board 24 is a control section for controlling the elements of the apparatus, and executes various types of controls, for example, turns power supply on or off.

The pulse adding section 25 vibrates the fuel oil produced in the stirring tanks 23 so that residue is easily removed. The residue is, for example, water which was left unreacted, impurities in the heavy oil or the like.

The Newton's separation tank 26 stores the fuel oil and drops the residue downward by the force of gravity, and thus extracts the fuel oil remaining in an upper part thereof.

The separation tank 27 further separates the residue from the fuel oil.

The precision filter 28 removes the residue from the fuel oil by a filter.

The finishing tank 29 stores the produced refined fuel oil.

The waste liquid tank 30 stores a waste liquid generated in the pulse adding section 25 and the Newton's separation tank 26.

Figure 3:
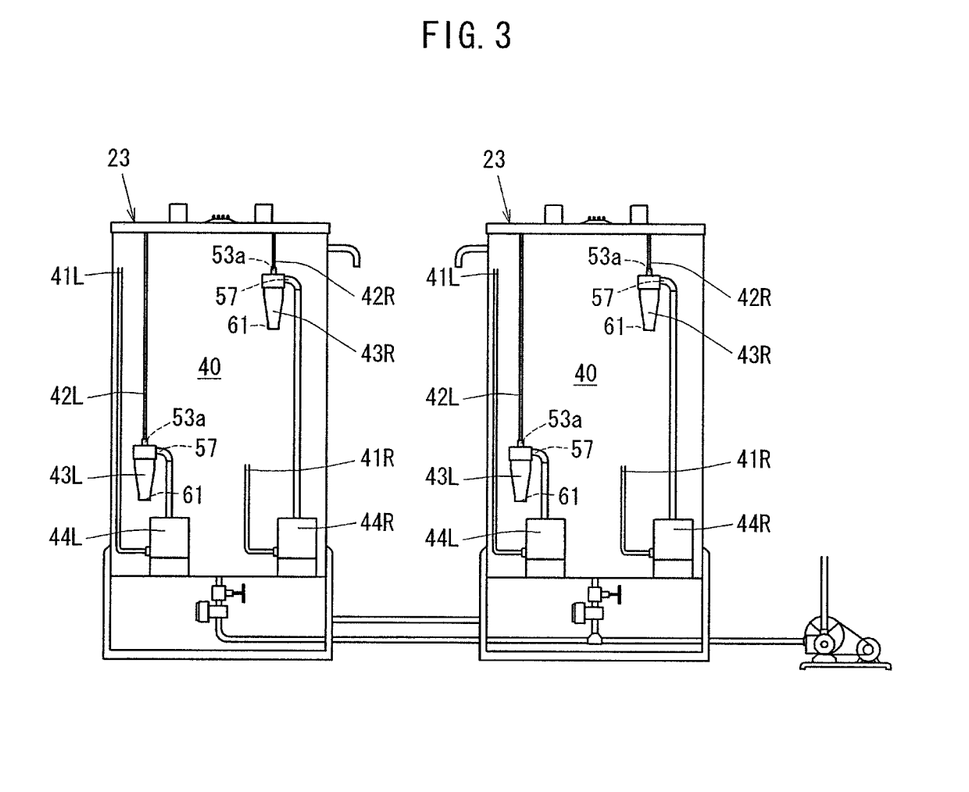
FIG. 3 is a structural view showing a structure of a stirring tank.

FIG. 3 is a structural view showing a structure of the stirring tanks 23.

The stirring tanks 23 each include a generally cylindrical stirring space 40. In the stirring space 40, stirrers 43 (43L, 43R) and pumps 44 (44L, 44R) are provided.

The stirrers 43 (43L, 43R) are suspended at a predetermined height in the stirring space 40 of the stirring tank 23 by cables 42 (42L, 42R).

Among the stirrers 43, the stirrer 43L shown left in the figure is provided in a lower part of the stirring space 40, and the stirrer 43R shown right in the figure is provided in an upper part of the stirring space 40. Thus, the stirrers 43 are located discretely up and down and also discretely left and right. The stirrers 43 are respectively connected to the pumps 44 (44L, 44R). From the pumps 44, fuel oil, enzyme water, or an enzyme water-oil mixture is supplied.

The pump 44L is connected to a pipe having a suction opening 41L in an upper part thereof. The pump 44L feeds the fuel oil, enzyme water, or enzyme water-oil mixture to the stirrer 43L, and thus circulates the fuel oil, enzyme water, or enzyme water-oil mixture in the stirring space 40 generally uniform.

The pump 44R is connected to a pipe having a suction opening 41R in a lower part thereof. The pump 44R feeds the fuel oil, enzyme water, or enzyme water-oil mixture to the stirrer 43R, and thus circulates the fuel oil, enzyme water, or enzyme water-oil mixture in the stirring space 40 generally uniform.

As each of the pumps 44L and 44R, it is preferable to use a 30 to 40 atmospheric pressure pump.

FIG. 4 illustrates a structure of the stirrer 43.

The stirrer 43 is a hollow metal element, and mainly includes a generally cylindrical head 51, a generally cylindrical neck 58 and an inverse conical body 59 which are continuous from the head 51, and a trailing end section 60 below the body 59.

On a central part of an upper surface of the head 51, a cylindrical central shaft 53 is provided. The central shaft 53 has an inflow hole 53a (see FIG. 5) running throughout the central shaft 53 in an up/down direction. The fuel oil, enzyme water, or enzyme water-oil mixture flows to the inside through the inflow hole 53a.

The head 51 has an inflow opening 57 in a part of a side surface thereof, through which the fuel oil, enzyme water, or enzyme water-oil mixture flows to the inside. The inflow opening 57 is a hole running from the outside to the inside of the head 51, and is surrounded by a cylindrical connection cover 55. The connection cover 55 has a thread groove 56 in an inner surface thereof, such that the pipe connected to the pump 44 is attachable thereto.

Figure 4A:
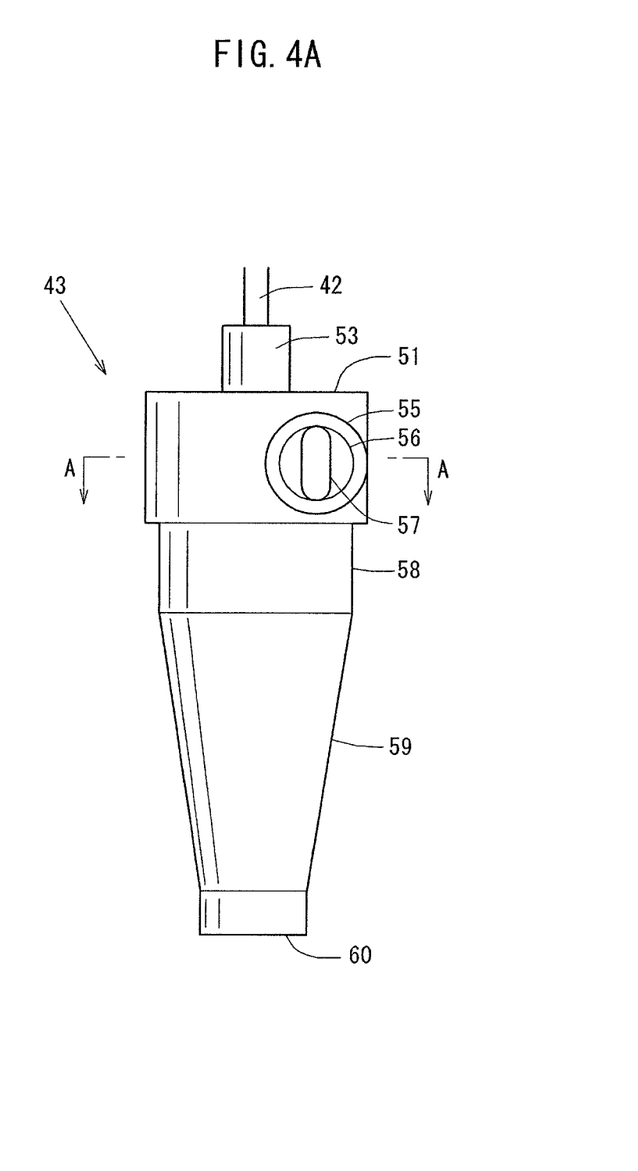
FIG. 4 illustrates a structure of a stirrer.
Figure 4B:
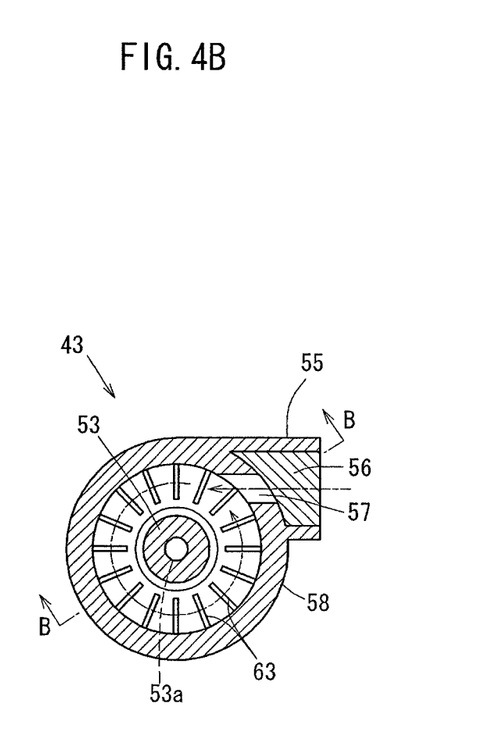

As shown in FIG. 4(B), which is a cross-sectional view of FIG. 4(A) along line A-A, the position of the inflow opening 57 and the orientation of the connection cover 55 are such that the fuel oil, enzyme water, or enzyme water-oil mixture flows toward the inner surface in an eccentric manner with respect to the center of the stirrer 43. Owing to this, fuel oil or the like flowing to the inside through the inflow opening 57 efficiently rotates around the cylindrical central shaft 53 as the rotation axis.

Figure 5:
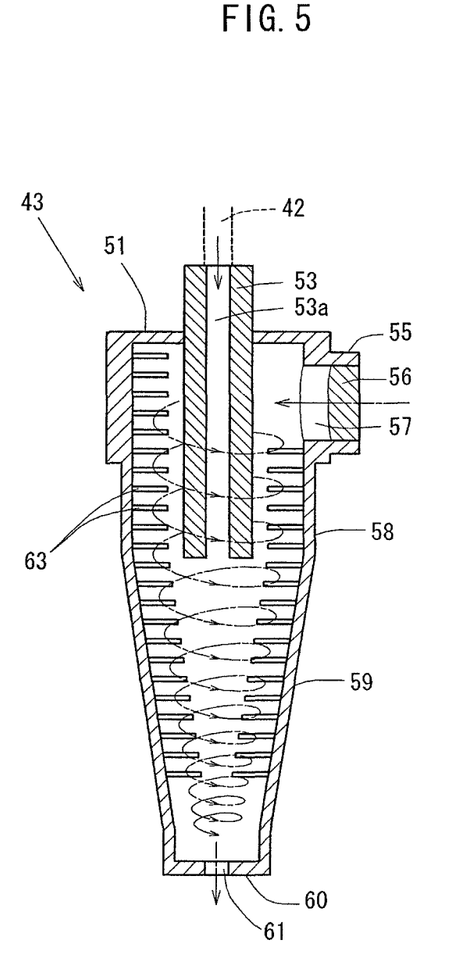
FIG. 5 is a vertical cross-sectional view showing the inside of the stirrer.

As shown in FIG. 5, which is a cross-sectional view of FIG. 4(B) taken along line B-B, a plurality of pins 63 stand on an inner surface of the stirrer 43. The plurality of pins 63 are located with an interval so as not to cross each other. For example, 55 to 80 pins having a diameter of 3 mm may be provided at an interval of about 10 mm.

In the trailing end section 60 of the stirrer 43, a discharge hole 61 is provided.

The stirrer 43 thus structured can stir oil and enzyme water efficiently to cause a decomposing reaction. In more detail, the fuel oil, enzyme water or enzyme water-oil mixture flowing to the inside through the inflow opening 57 rotates around the central shaft 53 while moving toward the discharge hole 61 with the rotation radius thereof being gradually decreased in a whirlwind manner. During this process, the fuel oil, enzyme water or enzyme water-oil mixture is stirred by the plurality of pins 63 provided in the stirrer 43. By the rotation in a whirlwind manner, a negative pressure is generated in a lower part of the central axis 53, which allows the fuel oil, enzyme water or enzyme water-oil mixture to flow to the inside through the inflow opening 53a.

Namely, the stirrer 43L shown in FIG. 3 mainly takes in the oil, suctioned from the suction opening 41L, by the pump 44L through the inflow opening 57, and mainly takes in the enzyme water through the inflow opening 53a, and stirs the oil and the enzyme water.

By contrast, the stirrer 43R mainly takes in the enzyme water, suctioned from the suction opening 41R, by the pump 44R through the inflow opening 57, and mainly takes in the oil through the inflow opening 53a, and stirs the oil and the enzyme water.

Owing to the stirrer 43, the enzyme water and the oil can collide against each other to be stirred in the water having a high pressure and thus can be reacted with each other.

While being stirred in the stirring tank 23 having the stirrer 43 for a predetermined time period (for example, about 15 to 20 minutes), the oil and the enzyme water stirred while moving in a whirlwind manner in the stirrer 43 contact each other 300 to 500 times. Thus, the hydrolysis reaction is promoted, and the molecules become smaller and the specific gravity is decreased.

Figure 6A:
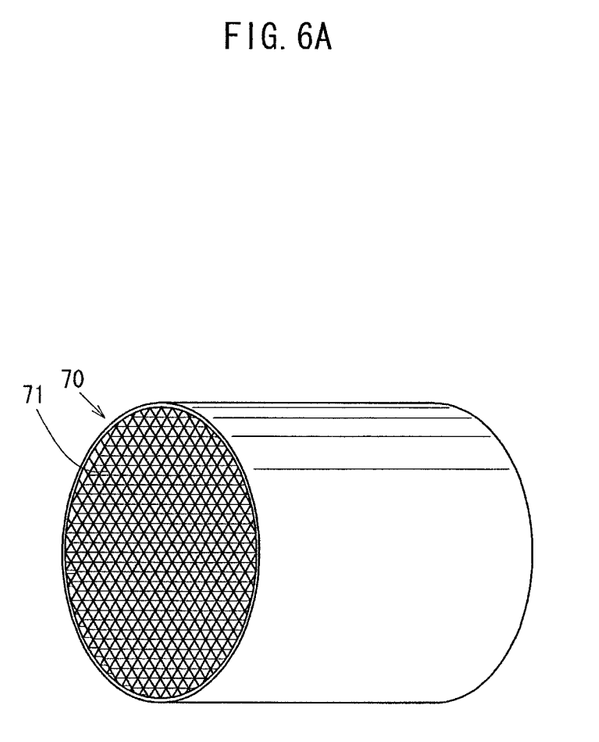
FIG. 6 illustrates a structure of a pulse filter and a structure of a precision filter.

FIG. 6(A) is an isometric view of a pulse filter 70 provided in the pulse adding section 25. The pulse filter 70 is provided between two line mixers, and allows the fuel oil to pass through holes formed in a lattice partition 71. The pulse adding section 25 (especially, the partition 71) is formed of a sintered ceramic material.

The partition 71 is slowly twisted inside like a screw, and vibrates the fuel oil flowing to the inside to promote the reaction. Owing to this, the fuel oil is put into a state where impurities are easily removed.

Figure 6B:
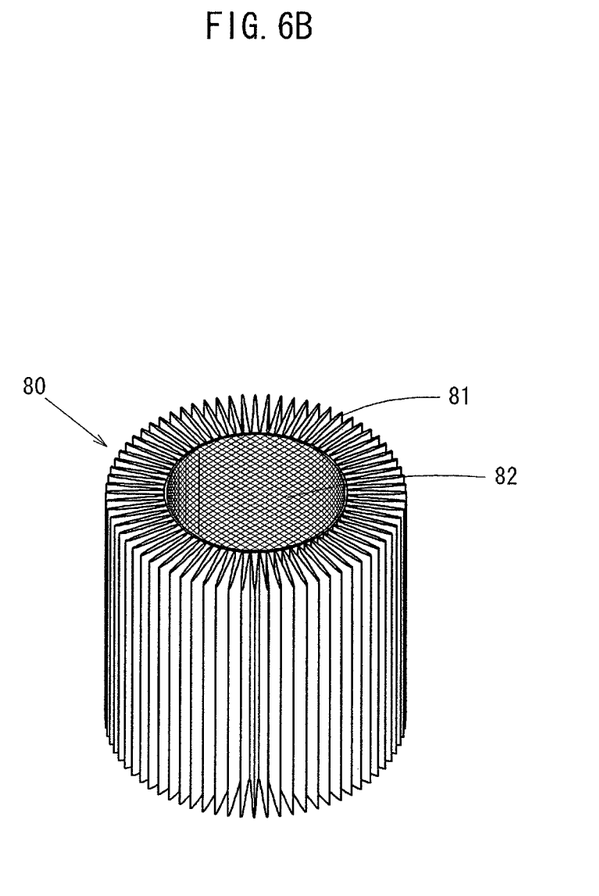

FIG. 6(B) is an isometric view of a precision filter 80 provided in the precision filter section 28.

The precision filter 80 includes a cylinder-like element 82 formed of a mesh material and a filter 81 provided around the cylinder-like element 82. The filter 81 radially expands from the center thereof. The fuel oil is allowed to pass through the filter 81 from outside toward the cylinder-like element 82, and thus impurities can be removed.

Figure 6C:
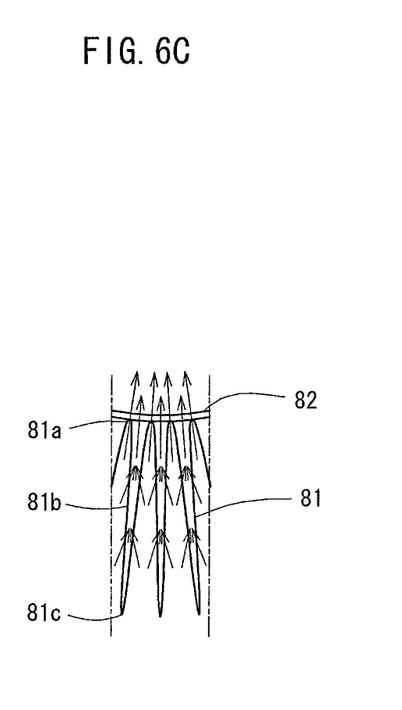

The filter 81 is provided radially. Therefore, as shown in FIG. 6(C), which is a partial enlarged view thereof, the fuel oil can pass the entirety of a plate-like face 81b of the filter 81 from a base-side end 81a to a tip-side end 81c. Therefore, even when impurities are accumulated at the base-side end 81a and it becomes difficult for the fuel oil to pass through the filter 81, the plate-like face 81b allows the fuel oil to pass with no problem and to remove the impurities.

Figure 7:
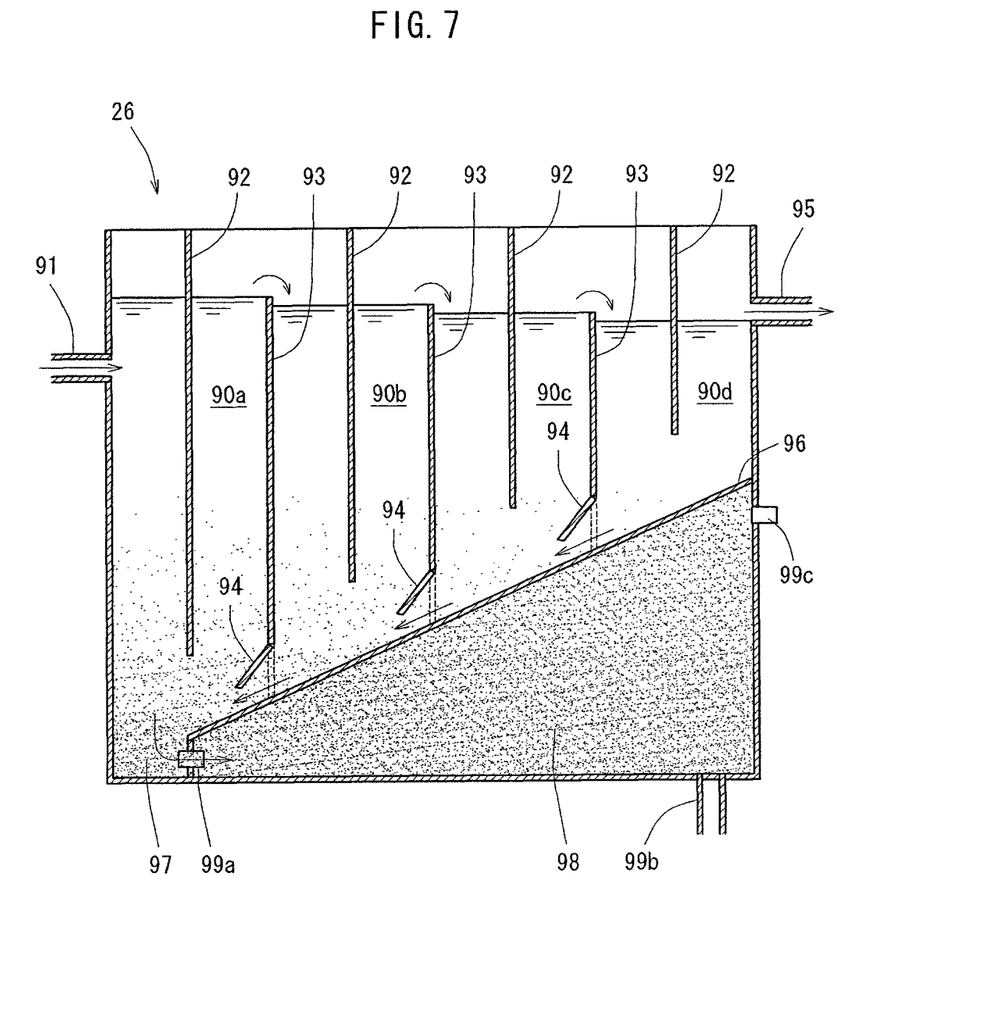
FIG. 7 is a cross-sectional view of a Newton's separation section.

FIG. 7 is a vertical cross-sectional view of the Newton's separation tank 26.

The Newton's separation tank 26 mainly includes an inclining plate 96 provided in the vicinity of a bottom section, and a plurality of higher-level plates 92 and a plurality of lower-level plates 93 which are alternately provided above the inclining plate 96. The Newton's separation tank 26 has a liquid inflow opening 91 for the connection with an element on the previous stage and a liquid discharge opening 95 for the connection with an element on the subsequent stage.

A space is provided between lower ends of the higher-level plates 92 and the inclining plate 96, so that the fuel oil can move forward and rearward.

Upper ends of the lower-level plate 93 are at a lower position that those of the higher-level plates 92, so that the stored fuel oil overflows and moves into the next storage section. The lower-level plates 93 each have a movable plate 94 at a lower end thereof, and a lower end of the movable plate 94 contacts the inclining plate 94.

The higher-level plates 92 and the lower-level plates 93 are arranged alternately in this order, and are provided such that lower ends thereof are gradually at a higher position along the inclination of the inclining plate 96.

Owing to this structure, the fuel oil flows to the inside through the liquid inflow opening 91 into a first storage section 90a. Impurities thereof are accumulated in a lower part thereof, and the refined fuel oil is stored in an upper part thereof and overflows into a second storage section 90b next to the first storage section 90a. This process is repeated from the first storage section 90a to a fourth storage section 90d, and the resultant clean fuel oil is discharged from the liquid discharge opening 95.

The impurities precipitated in the storage sections 90a through 90d move downward along the inclining plate 96. For this process, the movable plates 94 are opened to allow the impurities to move downward. The movable plates 94 are not opened in the opposite direction and so the impurities do not flow in the opposite direction.

The impurities moved downward along the inclining plate 96 are transferred from a recovery opening 97 to a recovery section 98 via a valve 99a and are recovered in the recovery section 98. The valve 99a is opened and closed intermittently. When the residue is stored in a certain amount, the valve 99a is opened to allow the residue to be recovered in the recovery section 98 and then is closed. Then, air is discharged via an air discharge valve 99c provided in an upper part of the recovery section 98. The impurities recovered in the recovery section 98 may be taken out via a recovery valve 99b and discarded.

By the enzyme water production apparatus 1 and the fuel production apparatus 2 described above, refined fuel oil obtained by a decomposing reaction of oil and enzyme water can be produced.

Figure 8:
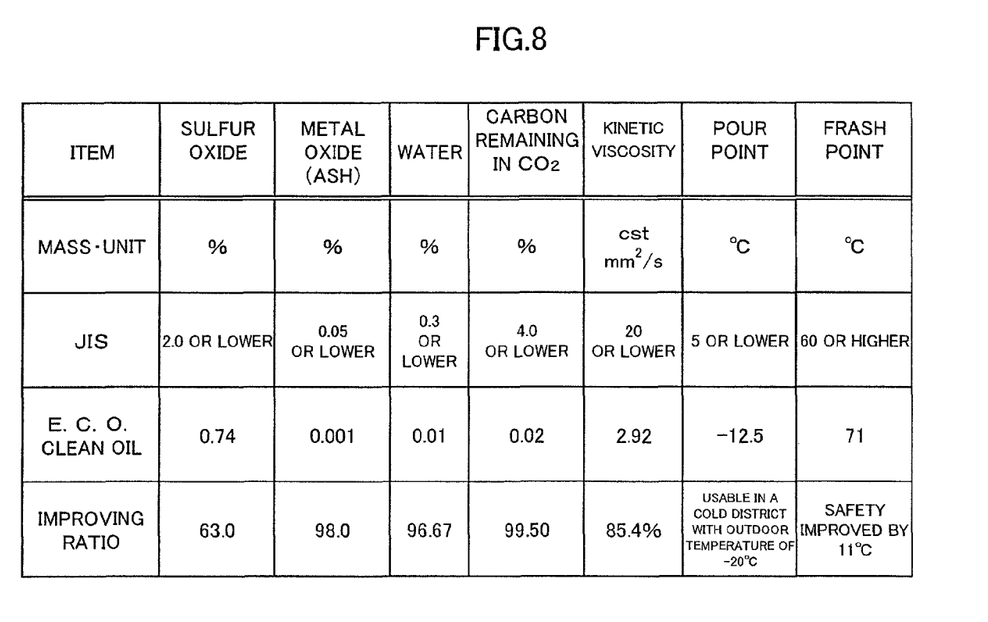
FIG. 8 provides characteristics of refined fuel oil.

Thus, as shown in FIG. 8, which is a table showing the characteristics, fuel oil contributing to the improvement of the fuel efficiency and the prevention of environmental destruction can be obtained.

The table shows the characteristics of the refined fuel oil produced by the enzyme water production apparatus 1 and the fuel production apparatus 2 using A heavy oil.

As shown in this table, in the refined fuel oil, $CO_2$ (carbon residue in $CO_2$) is reduced by 99.5%, sulfur oxide is reduced by 63.0%, metal oxide (ash) is reduced by 98.0%, and water is reduced by 96.67%.

Figure 9:
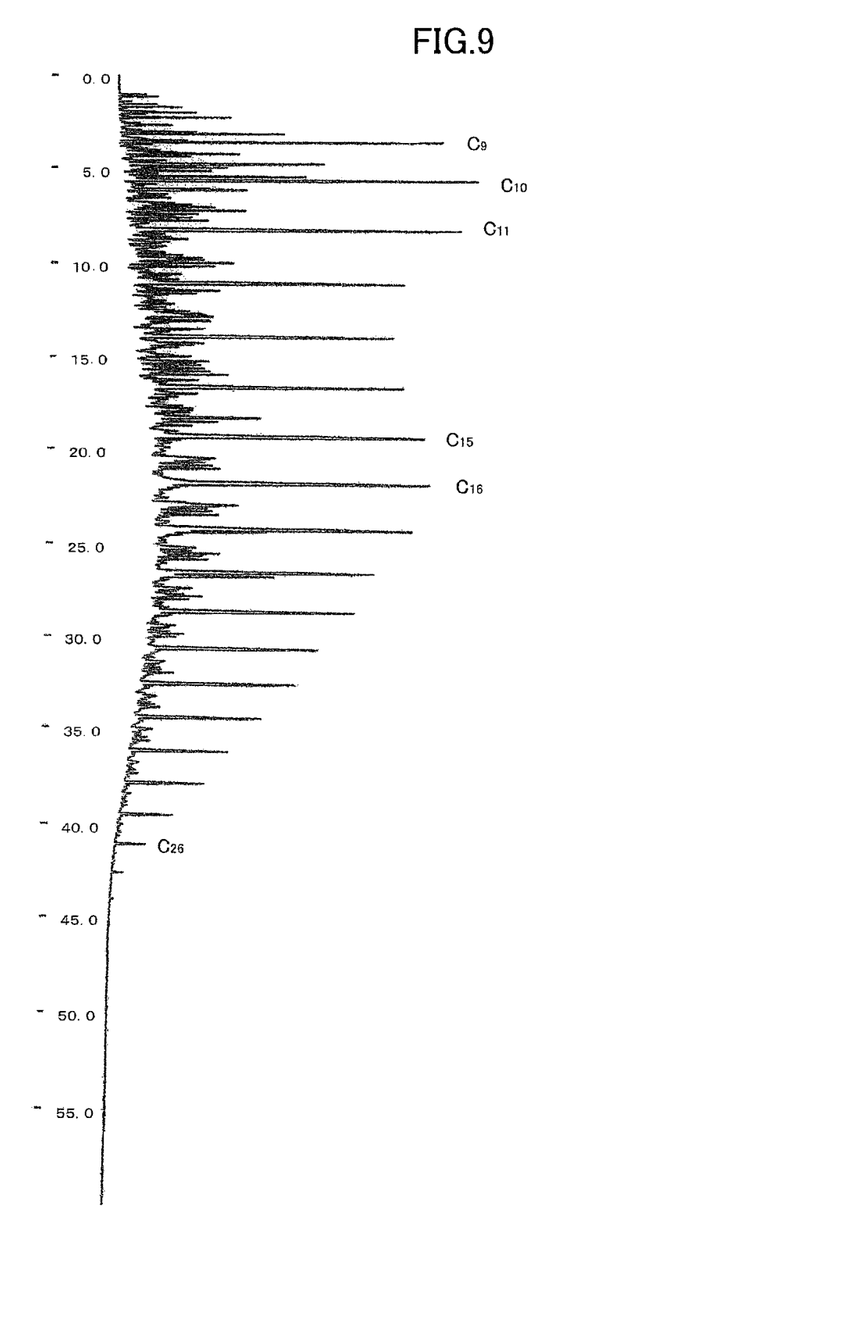
FIG. 9 is a graph showing results of a gas chromatography test of enzyme light oil refined from light oil by the fuel production apparatus.
Figure 10:
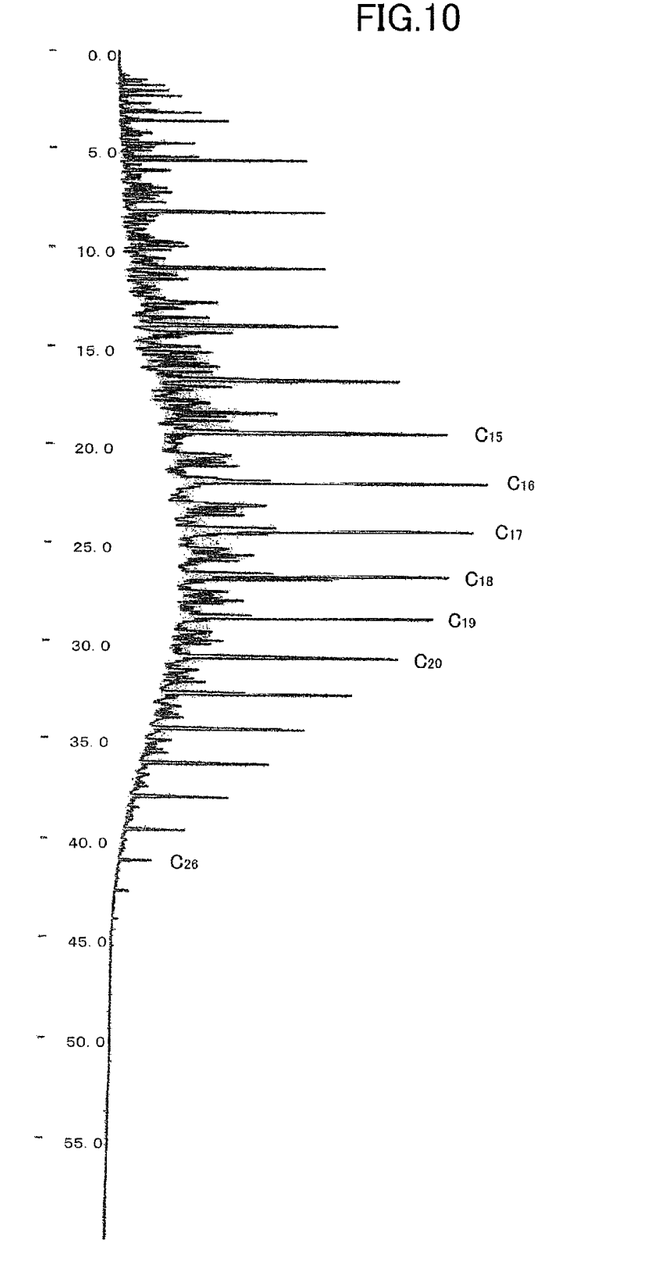
FIG. 10 is a graph showing results of a gas chromatography test of light oil as a material.

FIG. 9 is a graph showing results of a gas chromatography test conducted on enzyme light oil (clean oil) produced by the fuel production apparatus 2 described above using light oil as the material. FIG. 10 is a graph showing results of a gas chromatography test conducted on light oil which is the material before the reaction.

It is visually understood by comparing these graphs that the molecular weight of contained hydrocarbon is fractionated by the hydrolysis reaction caused by the natural plant enzyme containing lipase.

The chemical reaction based on which the present invention is made is sufficiently reproducible. In addition, the reaction of enzyme water and petroleum-based hydrocarbon oil is a mixing reaction, and the enzyme water itself is also combusted as fuel after the reaction.

As described above, refined fuel oil which is very clean, contributes to the prevention of environmental destruction, and has a high fuel efficiency can be produced. With the refined fuel oil, the absolute amount of oil to be used can be decreased by 20 to 30%, and the combustion efficiency can be improved by 20 to 25%. In total, the fuel can be saved by about 40 to 50%.

Owing to the enzyme power, the refined fuel oil can be used with no further treatment even in a cold district (for example, a district in which the temperature is decreased to −20° C.).

With the refined fuel oil, carbon does not to adhere to the engine or boiler, or the nozzle is not rusted, and so corrosion can be prevented. Therefore, general maintenance work is not necessary almost at all, which can reduce the maintenance costs.

The produced refined fuel oil is stabilized by the enzyme after the reaction, and so the oil component and the water component are not separated from each other even after a long time.

The produced refined fuel oil is highly transparent and the post-reaction water acts as the fuel. Therefore, the fuel efficiency can be raised.

The produced refined fuel oil does not generate soot or black smoke owing to the decomposing function of the enzyme. This can prevent the decline of the performance due to soot or black smoke remaining in a combustion engine for combusting the refined fuel oil.

The fuel production apparatus 2 can separate and thus remove $CO_2$, sulfur oxide, metal oxide and the like, which are hazardous substances, by the action of the enzyme.

The fuel production apparatus 2 can promote the hydrolysis reaction of oil by the enzyme owing to the efficient and uniform stirring operation provided by the stirrer 43.

Figure 11:
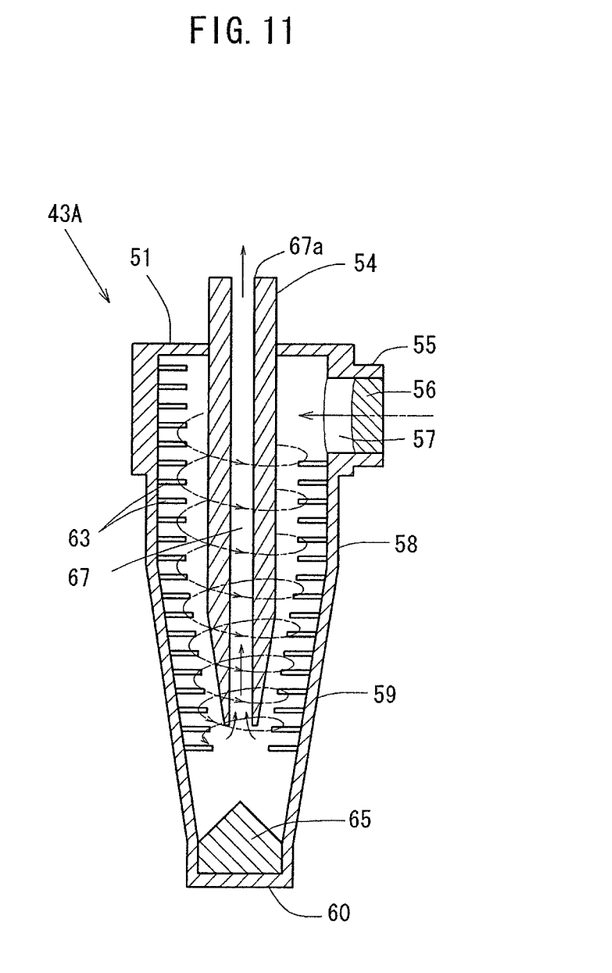
FIG. 11 is a vertical cross-sectional view showing a stirrer in another example.

As shown in FIG. 11, the stirrer 43 may be replaced with a different type of stirrer 43A. The stirrer 43A does not have a discharge hole in the trailing end section 60, and includes a central pipe 54 instead of the central shaft 53 provided in the example described above. The central pipe 54 has a cylindrical shape having a hollow section 67 inside. An upper end 67a of the hollow section 67 acts as a discharge opening for the fuel oil.

In the stirrer 43A having such a structure, enzyme water and oil flowing to the inside through the inflow opening 57 rotate while moving downward with the rotation radius thereof being gradually decreased in a whirlwind manner, and then move from a lower end to the upper end of the central pipe 54 and are discharged from the upper end.

The stirrer 43A also provides the same function and effect as those of the stirrer 43 described in the example above.

The elements of the present invention and the elements in the above-described embodiment correspond as follows.

The decomposing reaction tank of the present invention corresponds to the stirring tank 23 in the embodiment;

the residue removing section of the present invention corresponds to the pulse adding section 25, the Newton's separation tank 26, the separation tank 27 and the precision filter section 28 in the embodiment;

the stirrer of the present invention corresponds to the stirrers 43L, 43R and 43A in the embodiment;

the inflow opening of the present invention corresponds to the inflow opening 57 and the inflow hole 53a in the embodiment;

the discharge opening of the present invention corresponds to the discharge hole 61 in the embodiment; and the pins of the present invention correspond to the pins 63 in the embodiment.

The present invention is not limited to the structure of the above-described embodiment and can be carried out in various other embodiments.

INDUSTRIAL APPLICABILITY

The present invention is usable to improve the fuel efficiency of various types of oil, for example, A heavy oil, B heavy oil, C heavy oil, light oil, kerosene and the like.

DESCRIPTION OF THE REFERENCE NUMERALS

2 . . . fuel production apparatus; 23 . . . stirring tank; 25 . . . pulse adding section; 26 . . . . Newton's separation tank; 27 . . . separation tank; 28 . . . precision filter section; 43L, 43R, 43A . . . stirrer; 53a . . . inflow hole; 57 . . . inflow opening; 61 . . . discharge hole; 63 . . . pin.

What is claimed is:

1. A fuel production method for producing fuel oil, comprising:
    mixing a natural plant enzyme powder, containing about 98% by weight lipase and about 2% by weight cellulase, in water to create an enzyme water;
    mixing and reacting the enzyme water with petroleum-based hydrocarbon oil, in an amount such that the enzyme water is 30-40% by weight of a total amount of a mixed solution; and
    applying, as fuel oil, a solution produced by mixing and reacting the enzyme water with the petroleum-based hydrocarbon oil,
    wherein the enzyme water contains approximately 0.05% of the enzyme powder in weight.

2. A fuel production method according to claim 1, wherein the enzyme water further contains methanol mixed therein.

3. A fuel production method according to claim 1,
    wherein for mixing and reacting the enzyme water with the petroleum-based hydrocarbon oil, the enzyme water and the oil are caused to pass through a conical stirrer, having a plurality of pins provided therein, in a whirlwind manner.

4. A fuel production method according to claim 1,
    wherein residue is removed from the fuel oil to produce refined fuel oil.

* * * * *